US012622870B2

(12) United States Patent
Gordon

(10) Patent No.: US 12,622,870 B2
(45) Date of Patent: May 12, 2026

(54) BEVERAGE UNIT AND METHOD TO PROVIDE THE BEVERAGE UNIT

(71) Applicant: Bonafide Health, LLC, Harrison, NY (US)

(72) Inventor: Spencer Gordon, San Diego, CA (US)

(73) Assignee: Bonafide Health, LLC, Harrison, NY (US)

( * ) Notice: Subject to any disclaimer, the term of this patent is extended or adjusted under 35 U.S.C. 154(b) by 0 days.

(21) Appl. No.: 16/948,951

(22) Filed: Oct. 7, 2020

(65) Prior Publication Data

US 2022/0105032 A1     Apr. 7, 2022

(51) Int. Cl.
| | |
|---|---|
| *A61K 9/00* | (2006.01) |
| *A61K 31/7004* | (2006.01) |
| *A61K 47/12* | (2006.01) |
| *A61K 47/22* | (2006.01) |
| *A61K 9/08* | (2006.01) |

(52) U.S. Cl.
CPC ........ *A61K 9/0095* (2013.01); *A61K 31/7004* (2013.01); *A61K 47/12* (2013.01); *A61K 47/22* (2013.01); *A61K 9/08* (2013.01)

(58) Field of Classification Search
None
See application file for complete search history.

(56) References Cited

U.S. PATENT DOCUMENTS

| | | | | |
|---|---|---|---|---|
| 3,598,609 A | * | 8/1971 | Hoynak ................... | A23L 2/68 |
| | | | | 127/29 |
| 2002/0122847 A1 | * | 9/2002 | Nunes .................... | A23L 33/16 |
| | | | | 426/72 |
| 2003/0073643 A1 | | 4/2003 | Benedict | |
| 2003/0224094 A1 | * | 12/2003 | Bakal ................... | A23L 13/428 |
| | | | | 426/548 |
| 2005/0233050 A1 | * | 10/2005 | Chen ....................... | A23L 33/16 |
| | | | | 426/590 |
| 2009/0175843 A1 | * | 7/2009 | Gans ................... | A61K 31/375 |
| | | | | 424/732 |
| 2009/0180999 A1 | * | 7/2009 | Minatelli ............... | A61P 13/02 |
| | | | | 424/732 |
| 2011/0300266 A1 | * | 12/2011 | Rinaldi .................. | A23L 33/16 |
| | | | | 426/74 |

FOREIGN PATENT DOCUMENTS

| | | | |
|---|---|---|---|
| CN | 109846046 A | | 6/2019 |
| JP | 2011219469 A | | 4/2011 |
| JP | 2011254749 | * | 12/2011 |
| JP | 2012170342 A | | 9/2012 |
| WO | WO 2007/005521 | * | 1/2007 |

OTHER PUBLICATIONS

Uqora, Inc., Related Application, International PCT Application No. PCT/US2021/050747, International Search Report, Dated Jan. 5, 2022.

Uqora, Inc., Related Application, International PCT Application No. PCT/US2021/050747, Written Opinion of the Int'l Searching Authority, Dated Jan. 5, 2022.

Uqora, Inc., Related Application, International PCT Application No. PCT/US2021/050747, Notice of the Transmittal of the Int'l Search Report and the Written Opinion of the Int'l Searching Authority, Dated Jan. 5, 2022.

How to use D-Mannose | Pure and Me blog : Apr. 18, 2017 https://blog.pureandme.com/how-to-use-d-mannose/.

"D-mannose powder for prophylaxis of recurrent urinary tract infections in women: a randomized clinical trial," Kranjcec, B. et al., World Journal of Urology, 32-79-84 (2014) https://pubmed.ncbi.nlm.nih.gov/23633128/.

Buy Mingo UTI Prevention Drink Mix at Well.ca | Free Shipping $49+ in Canada. https://well.ca/products/mingo-uti-prevention-drink-mix_144268.html.

Related application, Uqora Inc., Int'l PCT Application No. PCT/US2021/050747, International Preliminary Report on Patentability. Dated: Mar. 28, 2023.

Uqora 10-pack dietary supplement, Supplement Facts label, 2015.

Uqora 10-pack dietary supplement package design with supplement facts, 2017.

Uqora 10-pack dietary supplement, Supplement Facts label, 2019.

* cited by examiner

*Primary Examiner* — Tigabu Kassa
(74) *Attorney, Agent, or Firm* — Arnall Golden Gregory LLP

(57) ABSTRACT

A beverage unit and method to provide the beverage unit, are disclosed herein. The beverage unit comprising: at least 1 gram of d-mannose; at least 6 ounces of liquid, wherein the at least 1 gram of d-mannose is dissolved and combined with the 6 ounces of liquid to create a solution; and a single-serving liquid package, wherein the solution is stored in the liquid package for single-use consumption.

10 Claims, 5 Drawing Sheets

50

70

BEVERAGE UNIT AND METHOD TO PROVIDE THE BEVERAGE UNIT

FIELD OF THE DISCLOSURE

The present disclosure relates to a beverage unit and method to provide the beverage unit.

BACKGROUND

A ready-to-consume beverage comprising a sufficient dosage of d-mannose combined with a minimum amount of a liquid (e.g., water) is not currently available to consumers for urinary tract infections (UTIs), flushing the urinary tract of bacteria, promoting urinary health, and/or other conditions or symptoms.

SUMMARY

One aspect of the present disclosure relates to a beverage unit for consumption by a consumer. The beverage unit may comprise at least 1 gram of d-mannose and at least 6 fluid ounces of a liquid. The d-mannose dissolved and combined in the liquid may create a solution. The beverage unit may comprise a single-serving liquid package that stores the solution for single-use consumption by the consumer. By providing the beverage unit, the consumer may consume the solution from the single-serving liquid package more easily after intercourse, other activity, or as needed to ensure effectiveness of the solution for UTIs, flushing the urinary tract of bacteria, promoting urinary health, and/or other conditions or symptoms and improve use.

These and other features, and characteristics of the present technology, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of 'a', 'an', and 'the' include plural referents unless the context clearly dictates otherwise.

DETAILED DESCRIPTION

Figure 1:
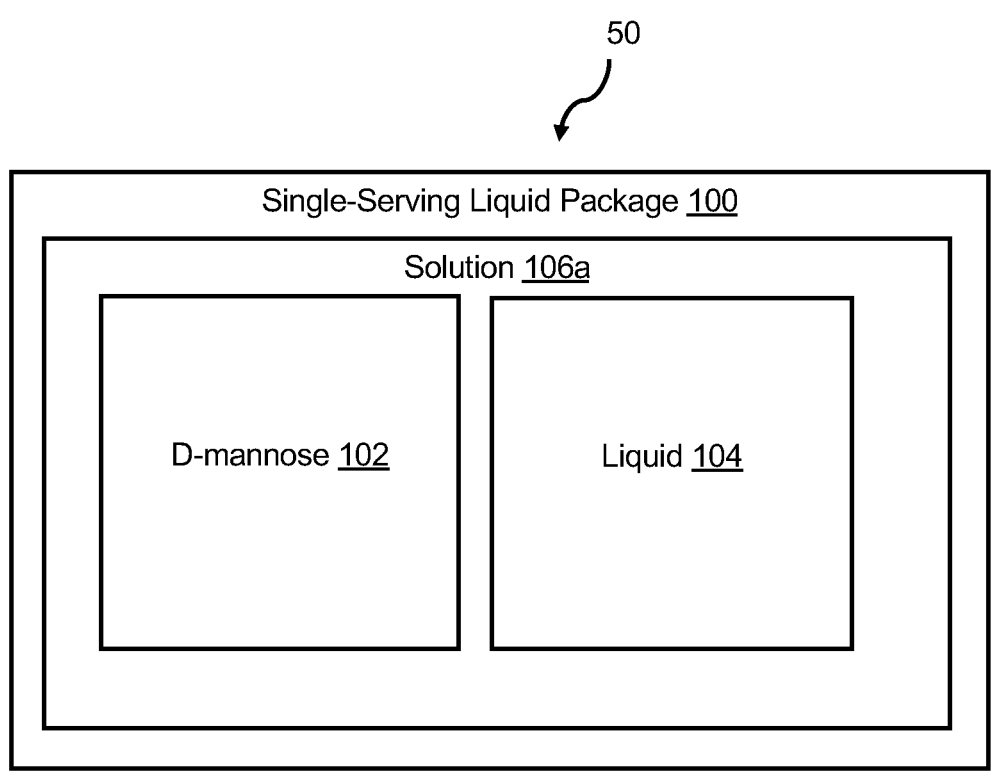
FIG. 1 illustrates a beverage unit, in accordance with one or more implementations.

FIG. 1 illustrates a beverage unit 50, in accordance with one or more implementations. Beverage unit 50 may comprise at least 1 gram of d-mannose 102, at least 6 fluid ounces of a liquid 104, a single-serving liquid package 100, and/or other elements. The at least 1 gram of d-mannose 102 may be dissolved and combined with the at least 6 fluid ounces of liquid 104 to create a solution 106*a*. Solution 106*a* may deliver the right dose of d-mannose 102 without requiring the consumer to combine d-mannose 102 with liquid 104. By providing solution 106*a* in single-serving liquid package 100 as beverage unit 50, a consumer may more easily consume solution 106*a*. Time of consumption, after intercourse or other activity that may introduce bacteria to the urinary tract, may be important for effectiveness of solution 106*a* for UTIs and/or other conditions or symptoms. Thus, beverage unit 50 may improve compliance of consumers to consume solution 106*a*.

In some implementations, solution 106*a* may comprise of between about 1 gram and about 5 grams of d-mannose 102. In some implementations, the grams of d-mannose 102 in solution 106*a* may be greater than about 1 gram, 2 grams, 3 grams, 4 grams, 5 grams, may be less than about, and/or may be within a range bounded at the upper end by any weight in the former listing of weights and bounded at the lower end by any weight in the latter listing of weights.

In some implementations, solution 106*a* may comprise of about 6 to about 16 fluid ounces of liquid 104. In some implementations, the fluid ounces of liquid 104 in solution 106*a* may be greater than about 6 fluid ounces, 8 fluid ounces, 9 fluid ounces, 10 fluid ounces, 11 fluid ounces, 12 fluid ounces, 13 fluid ounces, 14 fluid ounces, 15 fluid ounces, 16 fluid ounces, may be less than about, and/or may be within a range bounded at the upper end by any volume in the former listing of volumes and bounded at the lower end by any volume in the latter listing of volumes. In some implementations, solution 106*a* may comprise of 16 fluid ounces of liquid 104. In some implementations, liquid 104 may be water, juice, one or more concentrates, combinations thereof, and/or other liquids. Combining d-mannose 102 with liquid 104 may ensure that solution 106*a* is consumed with at least a minimum amount of liquid (e.g., water) for maximum function.

The use of the term "about" applies to all numeric values, whether or not explicitly indicated. This term generally refers to a range of numbers that one of ordinary skill in the art would consider as a reasonable amount of deviation to the recited numeric values (i.e., having the equivalent function or result). For example, this term can be construed as including a deviation of ±1 grams of the given numeric value provided such a deviation does not alter the end function or result of the value. Therefore, a value of about 2 grams can be construed to be a range from 1 gram to 3 grams. Furthermore, a range may be construed to include the start and the end of the range. For example, a range of 2 grams to 5 grams (i.e., range of 2-5 grams) includes 2 grams and also includes 5 grams, as well as grams in between 2 grams and 5 grams, unless explicitly stated otherwise herein.

As another example, this term can be construed as including a deviation of ±2 fluid ounces of the given numeric value provided such a deviation does not alter the end function or result of the value. Therefore, a value of about 10 fluid ounces can be construed to be a range from 8 fluid ounces to 12 fluid ounces. Furthermore, a range may be construed to include the start and the end of the range. For example, a range of 8 fluid ounces to 10 fluid ounces (i.e., range of 8-10 fluid ounces) includes 8 fluid ounces and also includes 10 fluid ounces, as well as fluid ounces in between 8 fluid ounces and 10 fluid ounces, unless explicitly stated otherwise herein.

Beverage unit 50 may comprise a single-serving liquid package 100. Solution 106*a* may be stored in single-serving liquid package 100 for single-use consumption by a consumer. Single-serving liquid package 100 may be a glass package, a plastic package (e.g., flexible plastic, rigid plastic, Polyethylene terephthalate (PET) plastic), a metal package (e.g., a can), paperboard package, pouch package (i.e., metal foil, propylene, polyester), combinations thereof, and/or other single-serving liquid package. In some implementations, single-serving liquid package 100 may allow beverage unit 50 to be refrigerated. In some implementations, single-serving liquid package 100 may allow beverage unit 50 to be unrefrigerated.

Figure 2:
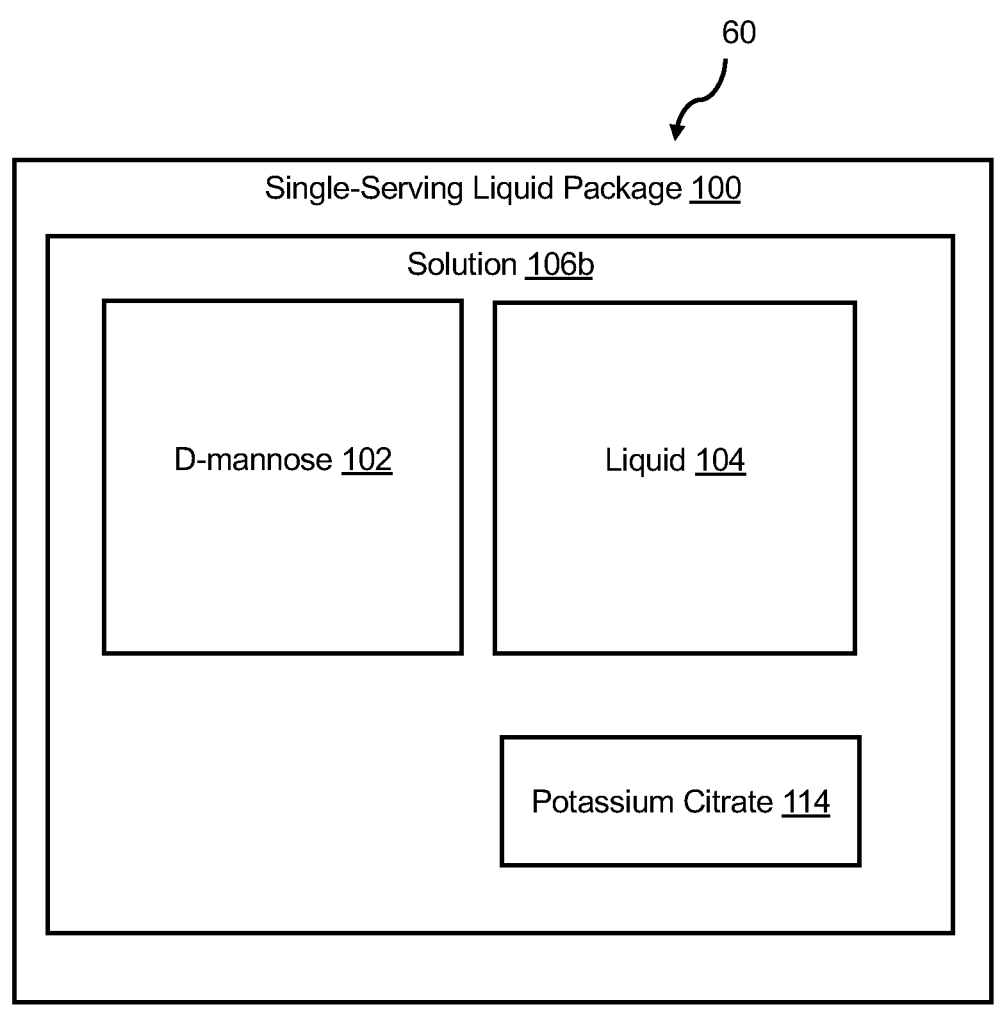
FIG. 2 illustrates a beverage unit, in accordance with one or more implementations.

FIG. 2 illustrates a beverage unit 60, in accordance with one or more implementations. Beverage unit 60 may comprise of the at least 1 gram of d-mannose 102, the at least 6 fluid ounces of a liquid 104, and/or other elements and the various implementations described thereof in FIG. 1 that when combined create solution 106*b*, similar to solution 106*a* of FIG. 1, stored in the single-serving liquid package 100 (same as FIG. 1). Solution 106*b* of beverage unit 60 may further comprise potassium citrate 114, and/or other vitamins, and/or other elements.

In some implementations, solution 106*b* may include between about 1 and about 6 grams of potassium citrate 114. In some implementations, the grams of potassium citrate 114 in solution 106*b* may be greater than about 1 gram, 2 grams, 3 grams, 4 grams, 6 grams, may be less than about, and/or may be within a range bounded at the upper end by any weight in the former listing of weights and bounded at the lower end by any weight in the latter listing of weights.

Figure 3:
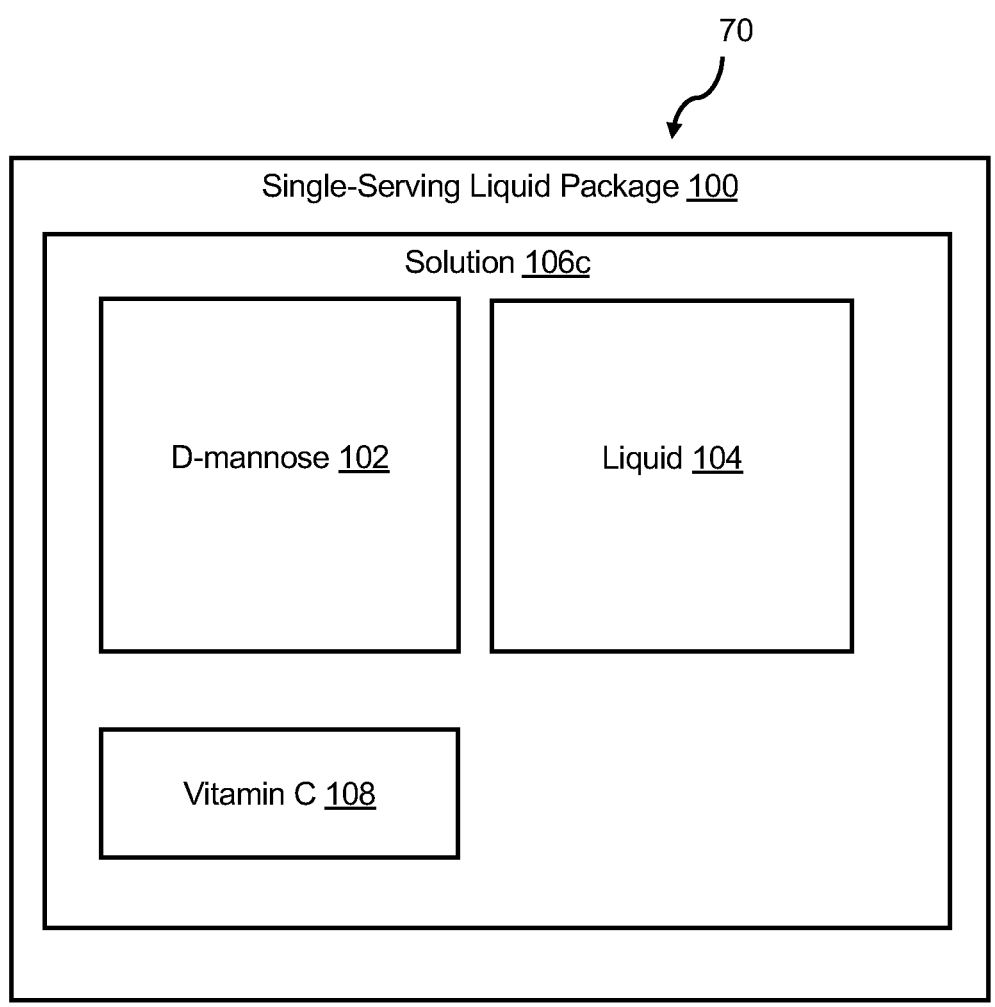
FIG. 3 illustrates a beverage unit, in accordance with one or more implementations.

FIG. 3 illustrates a beverage unit 70, in accordance with one or more implementations. Beverage unit 70 may comprise of the at least 1 gram of d-mannose 102, the at least 6 fluid ounces of a liquid 104, and/or other elements and the various implementations described thereof in FIG. 1 that when combined create solution 106*c*, similar to solution 106*a* of FIG. 1, stored in the single-serving liquid package 100 (similar to FIGS. 1 and 2). Solution 106*c* may further comprise vitamin C 108, and/or other vitamins, and/or other elements.

In some implementations, solution 106*c* may include between about 60 milligrams and about 2000 milligrams of vitamin C 108. In some implementations, the milligrams of vitamin C 108 in solution 106*c* may be greater than about 60 milligrams, 100 milligrams, 500 milligrams, 1000 milligrams, 1200 milligrams, 1500 milligrams, 2000 milligrams, may be less than about, and/or may be within a range bounded at the upper end by any weight in the former listing of weights and bounded at the lower end by any weight in the latter listing of weights.

The term "about" can be construed as including a deviation of ±10 milligrams of the given numeric value provided such a deviation does not alter the end function or result of the value. Therefore, a value of about 60 milligram can be construed to be a range from 50 milligrams to 70 milligrams. Furthermore, a range may be construed to include the start and the end of the range. For example, a range of 60 milligram to 2000 milligram (i.e., range of 60-2000 milligram) includes 60 milligram and also includes 2000 milligram, as well as milligram in between 60 milligram and 2000 milligram, unless explicitly stated otherwise herein.

Figure 4:
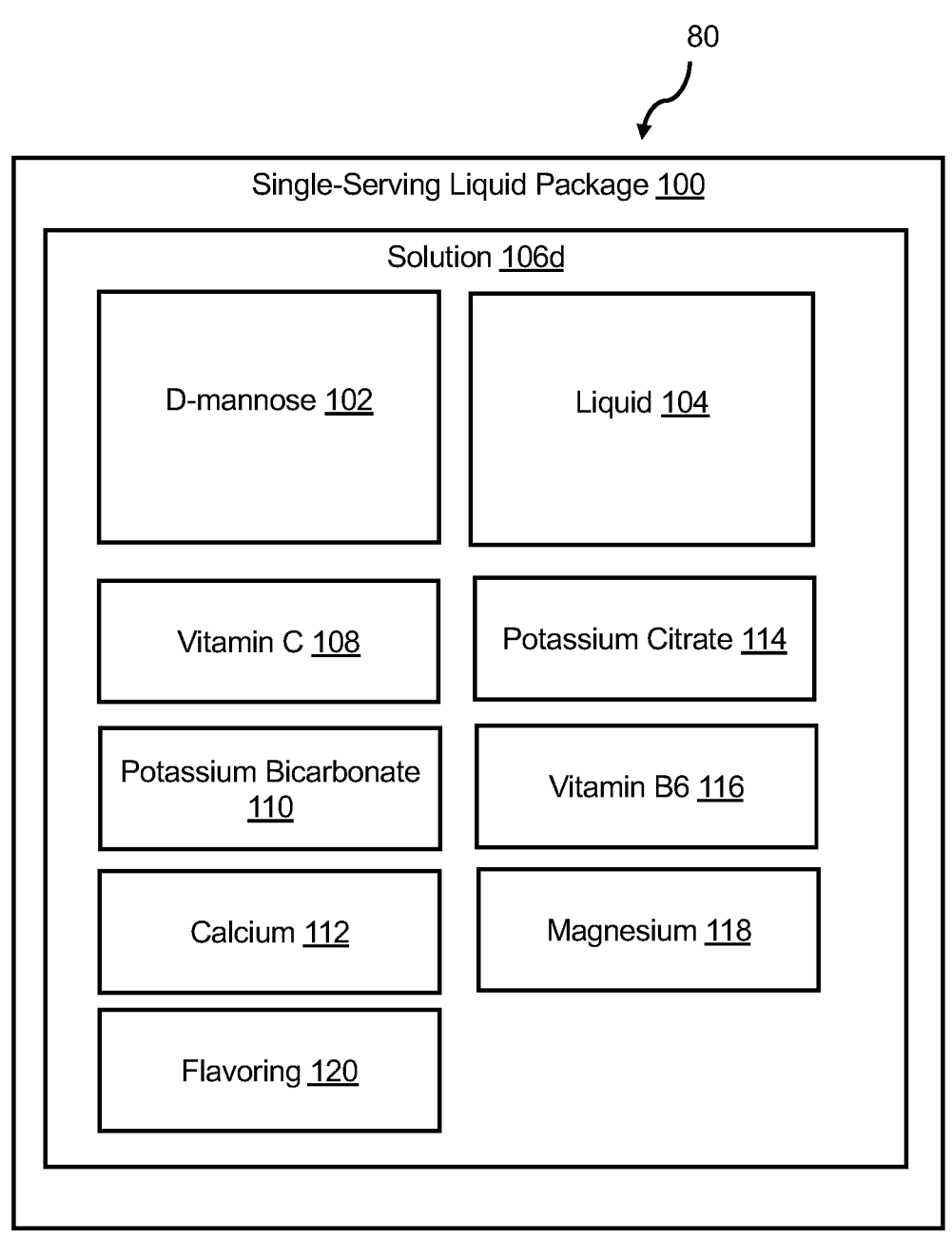
FIG. 4 illustrates a beverage unit, in accordance with one or more implementations.

FIG. 4 illustrates a beverage unit 80, in accordance with one or more implementations. Beverage unit 70 may comprise of the at least 1 gram of d-mannose 102, the at least 6 fluid ounces of a liquid 104, and/or other elements and the various implementations described thereof in FIG. 1-3 that when combined create solution 106*d*, similar to solution 106*a-c* of FIG. 1-3, stored in the single-serving liquid package 100 (same as FIG. 1-3). Solution 106*d* may further comprise potassium bicarbonate 110, calcium 112, vitamin B6 116, magnesium 118, flavoring 120, and/or other vitamins, and/or other elements in addition to potassium citrate 114 of FIG. 2 and vitamin C 108 of FIG. 3.

In some implementations, solution 106*d* may include about 1 gram to about 5 grams of potassium bicarbonate 110. In some implementations, the grams of potassium bicarbonate 110 in solution 106*d* may be greater than about 1 gram, 2 grams, 3 grams, 4 grams, 5 grams, may be less than about, and/or may be within a range bounded at the upper end by any weight in the former listing of weights and bounded at the lower end by any weight in the latter listing of weights.

In some implementations, solution 106*d* may include about 25 milligrams to about 500 milligrams of calcium 112. In some implementations, the milligrams of calcium 112 in solution 106*d* may be greater than about 25 milligrams, 100 milligrams, 250 milligrams, 500 milligrams, may be less than about, and/or may be within a range bounded at the upper end by any weight in the former listing of weights and bounded at the lower end by any weight in the latter listing of weights.

In some implementations, solution 106*d* may include about 10 milligrams to about 100 milligrams of vitamin B6 116. In some implementations, the milligrams of vitamin B6 116 in solution 106*d* may be greater than about 10 milligrams, 50 milligrams, 100 milligrams, may be less than about, and/or may be within a range bounded at the upper end by any weight in the former listing of weights and bounded at the lower end by any weight in the latter listing of weights.

In some implementations, solution 106*d* may include about 10 milligrams to about 100 milligrams of magnesium 118. In some implementations, the milligrams of magnesium 118 in solution 106*d* may be greater than about 10 milligrams, 50 milligrams, 100 milligrams, may be less than about, and/or may be within a range bounded at the upper end by any weight in the former listing of weights and bounded at the lower end by any weight in the latter listing of weights.

In some implementations, solution 106*d* of beverage unit 80 may further comprise flavoring 120. Flavoring 120 may include natural flavoring, artificial flavoring, natural sugar, artificial sugar, salt, and/or other flavoring. By way of non-limiting example, flavoring 120 may provide a fruit taste (e.g., strawberry, blueberry, mango, orange, apple, banana, etc.), a sweet taste, a tart taste, and/or other tastes.

Figure 5:
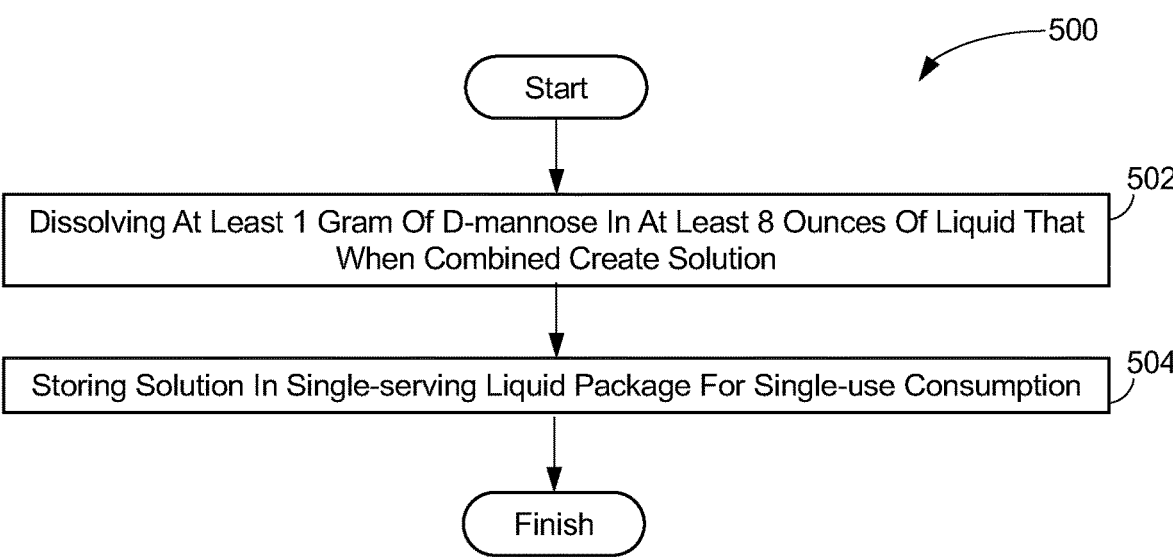
FIG. 5 illustrates a method to provide a beverage unit, in accordance with one or more implementations.

FIG. 5 illustrates a method 500 to provide a beverage unit, in accordance with one or more implementations. The operations of method 500 presented below are intended to be illustrative. In some implementations, method 500 may be accomplished with one or more additional operations not described, and/or without one or more of the operations discussed. Additionally, the order in which the operations of method 500 are illustrated in FIG. 5 and described below is not intended to be limiting.

An operation 502 may include dissolving at least 1 gram of d-mannose in at least 6 fluid ounces of liquid that when combined create a solution.

An operation 504 may include storing the solution in a single-serving liquid package for single-use consumption.

Although the present technology has been described in detail for the purpose of illustration based on what is currently considered to be the most practical and preferred implementations, it is to be understood that such detail is solely for that purpose and that the technology is not limited to the disclosed implementations, but, on the contrary, is intended to cover modifications and equivalent arrangements that are within the spirit and scope of the appended claims. For example, it is to be understood that the present technology contemplates that, to the extent possible, one or more features of any implementation can be combined with one or more features of any other implementation.

What is claimed is:

1. A beverage unit comprising:
a solution consisting of:
more than 1 gram of d-mannose;
an amount of at least one salt selected from the group consisting of a citrate salt and a bicarbonate salt;
an amount of vitamin C;
6 fluid ounces to 16 fluid ounces of liquid, and
optionally, at least one of a flavoring, an amount of at least one other vitamin, an amount of a sweetener; and
a single-serving liquid package, wherein the solution is stored in the liquid package for single-use consumption.

2. The beverage unit of claim 1, wherein the amount of the d-mannose is 2 grams.

3. The beverage unit of claim 1, wherein the amount of the d-mannose is at most 5 grams.

4. The beverage unit of claim 1, wherein the amount of the liquid is 8-10 fluid ounces.

5. The beverage unit of claim 1, wherein the amount of the liquid is 10-12 fluid ounces.

6. The beverage unit of claim 1, wherein the amount of the liquid is 16 fluid ounces of the liquid.

7. The beverage unit of claim 1, wherein the liquid is water.

8. The beverage unit of claim 1, wherein the at least one salt is a citrate salt and the citrate salt is potassium citrate.

9. The beverage unit of claim 1, wherein the solution is free of a sweetener.

10. The beverage unit of claim 1, wherein the beverage unit is stored in an unrefrigerated state.

* * * * *